United States Patent [19]

Fujiwara

[11] 4,281,660
[45] Aug. 4, 1981

[54] METHOD FOR FIXING PERVENOUS ELECTRODE IN ATRIAL PACING AND DEVICE THEREFOR

[76] Inventor: Tugumasa Fujiwara, 1-11 Sakuragaoka 4 chome, Kushiro-shi, Hokkaido, Japan

[21] Appl. No.: 32,234

[22] Filed: Apr. 20, 1979

[30] Foreign Application Priority Data

Oct. 18, 1978 [JP] Japan .................................. 53/127266

[51] Int. Cl.³ .......................... A61B 5/04; A61N 1/04
[52] U.S. Cl. ................................ 128/642; 128/419 P; 128/785
[58] Field of Search ........................ 128/642, 784–786, 128/419 P

[56] References Cited

U.S. PATENT DOCUMENTS

| 4,057,067 | 11/1977 | Lajos ..................................... 128/785 |
| 4,103,690 | 8/1978 | Harris ............................... 128/786 X |
| 4,136,703 | 1/1979 | Wittkampf ........................ 128/419 P |

FOREIGN PATENT DOCUMENTS 2365351  4/1978  France .................................. 128/419 P Primary Examiner—Lee S. Cohen
Attorney, Agent, or Firm—Oblon, Fisher, Spivak, McClelland & Maier

[57] ABSTRACT

A method for the fixation of a permanent pervenous electrode for atrial pacing, comprising the steps of inserting an inspection catheter into the right atrium to determine the optimum position inside the right atrium for the fixation of a pervenous electrode, causing a guidewire slidably built in the inspection catheter to be forced out and allowed to form a loop along the endocardium of the right atrium, inserting into the right atrium an induction steel wire via a double lumen needle pierced through the chest wall in the direction of the loop of guidewire, causing the loop to tighten around and catch firm hold of the induction steel wire and withdrawing completely the inspection catheter while the induction steel wire is held in a state caught fast in the contracted loop of guidewire at the end of the catheter, replacing the inspection catheter with the permanent pervenous electrode, drawing the steel wire backwardly and thereby introducing the pervenous electrode into the right atrium and suturally fixing the pervenous electrode at the aforementioned optimum position.

3 Claims, 12 Drawing Figures

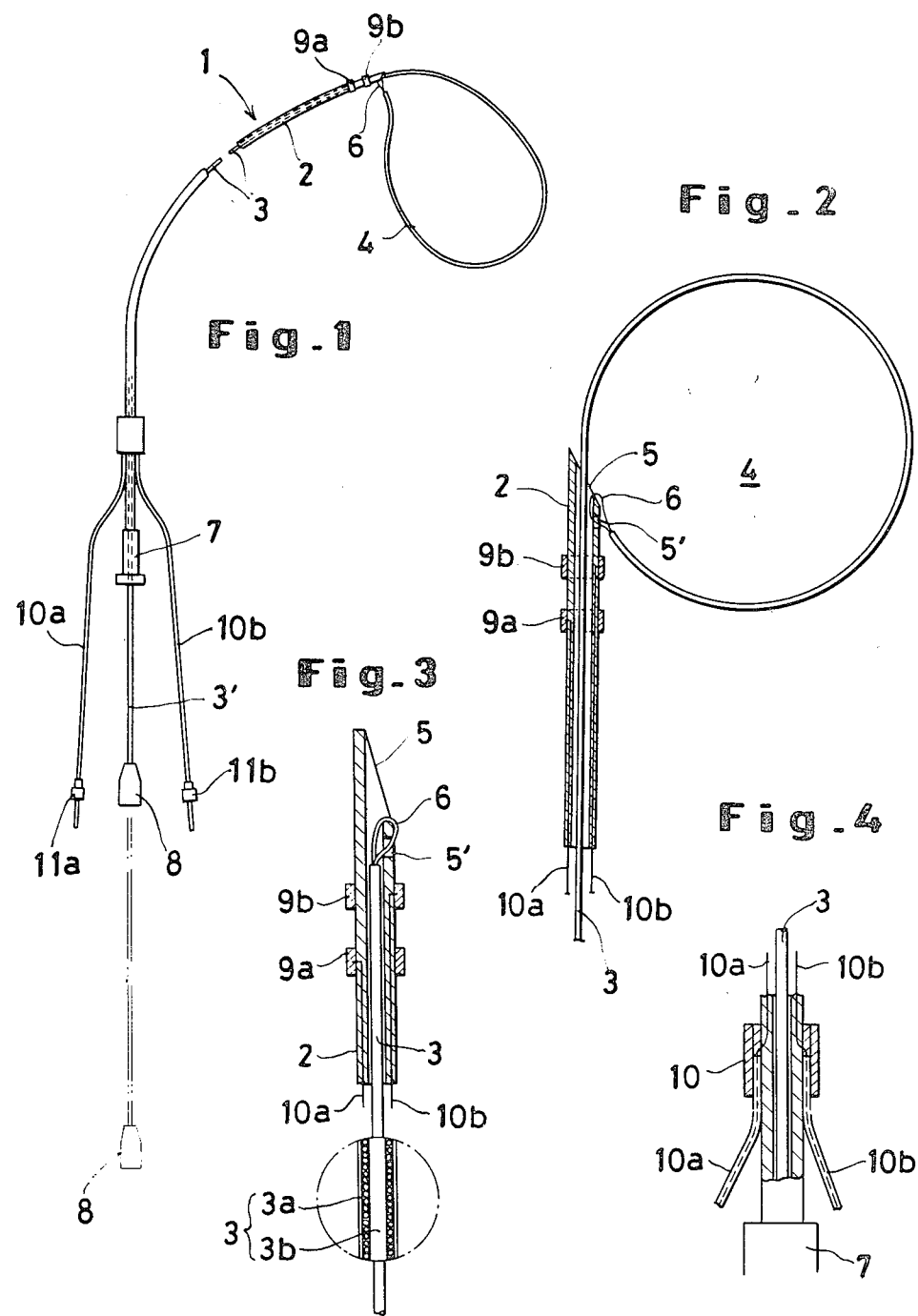

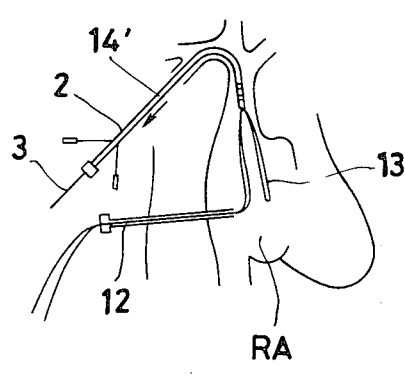
Fig_9
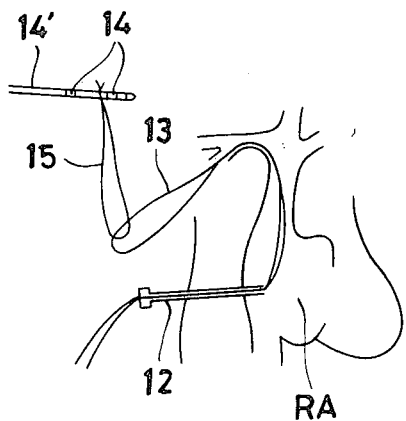
Fig_10
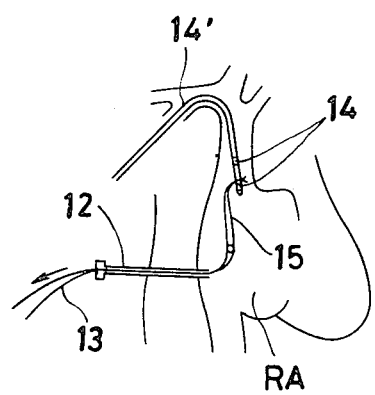
Fig_11
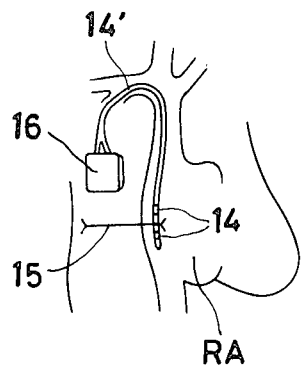
Fig_12

METHOD FOR FIXING PERVENOUS ELECTRODE IN ATRIAL PACING AND DEVICE THEREFOR

BACKGROUND OF THE INVENTION

This invention relates to a method and an inspection catheter for easy and safe fixation of pervenous electrodes at the optimum position within the right atrium for treatment of arrhythmia through the electrical stimulation of the affected heart.

The pacemakers of the kind which require that electrodes for delivering rhythmical electrical stimuli be fixed within the atrium include the P-synchronized pacemaker, the bifocal demand pacemaker, the fixed-rate pacemaker, the demand pacemaker and the radiofrequency induced atrial pacemaker.

The electrodes for delivering electrical stimulating pulses from pacemakers to the atrium are broadly grouped by the method of fixation thereof into two types: Myocardial electrodes which are fixed as by thoracotomy and allowed to generate electrical stimuli epicardially and pervenous electrodes which are fixed after insertion through the incised subclavian vein and allowed to generate electrical stimuli endocardially. The myocardial electrodes are highly susceptible to surgical incursions and, therefore, are not suitable for use on senile patients and poor risk patients unable to endure surgery. The present invention relates to a method for the endocardial stimulation by use of a pervenous electrode.

The methods which have heretofore been developed for the fixation of pacemaker pervenous electrodes in the right atrium include those involving insertion of a J-shaped lead or anchored electrodes in the right atrial appendages and those involving insertion of a pair of pacemaker pervenous electrodes in the coronary sinuses, for example. In all these conventional methods, since the electrodes are not sutured to the endocardium, there is a possibility of the electrodes being detached from the positions of the endocardium where they were initially fixed, with the result that the pacemakers will fail to provide required pacing and sensing actions.

The inventor, therefore, performed clinical trials in search of a way of improving the conventional methods described above. On the basis of the outcomes of the clinical trials, the inventor perfected a method for safe fixation of the pervenous electrodes at the optimum position within the right atrium to provide required atrial pacing in a given case. At the 30th general meeting of the Japanese Association for Thoracic Surgery held on Sept. 25, 1977, the inventor published this method. He further published this method in medical journals, specifically in the February, 1978 and August, 1978 issues of the "Japanese Journal of Thoracic Surgery" and in the "Journal of the Japanese Association for Thoracic Surgery", Vol. 26, No. 8.

The gist of the publication is as follows:

The subclavian fossa of a given patient is subjected to skin incision to expose the right cepharic vein and a catheter with a pair of inspection electrodes for potential detection is inserted through the vein into the right atrium. The right atrium is explored with the inserted catheter to determine the optimum position of a permanent pervenous pacemaker electrode through measurement of the stimulating thresholds and endocardial potentials in the anterior and lateral walls inside the right atrium. When the optimum position for fixing the pacemaker electrode is found, the catheter for potential detection is extracted. Then in the same manner, a guide catheter consisting of an outer tube and guidewire slidably built in the outer tube is inserted into the right atrium. The rear end of the guidewire is pushed into the outer tube to form at the predetermined optimum position a loop of the guidewire at the leading end of the outer tube under fluoroscopic observation. Thereafter, a double lumen needle is pierced through the chest wall in the direction of the formed loop of the guidewire inside the right atrium under fluoroscopic observation. After a doubly folded fine steel wire is inserted into the right atrium through the double lumen needle, the guidewire is drawn back through the outer tube to contract the loop of the guidewire thereby to catch firm hold of the inserted end of the steel wire and then, the guide catheter is extracted together with the steel wire. The guide catheter thus extracted is released from the steel wire and instead, the pervenous pacemaker electrode is connected to the steel wire by means of a sutural thread. The steel wire is next caused to introduce the pacemaker electrode into the interior of the right atrium by pulling outwardly the rear ends of the steel wire remaining the outer side of the lumen needle so as to pull the sutural thread out of the lumen needle. When the pacemaker electrode reaches the predetermined optimum position, the double lumen needle is removed from the chest wall and the sutural thread is sutured on the subcutaneous tissue for thereby fixing the pacemaker electrode in the endocardium of the atrium. Even this method unfortunately requires more time and labor and higher surgical skill.

An object of the present invention, therefore, is to provide a method and an inspection catheter for ready fixation of the pervenous pacemaker electrode at the optimum position within the atrium, with ample saving in the time and labor required for the fixation of the pacemaker electrode in the endocardium in the atrial pacing.

SUMMARY OF THE INVENTION

To accomplish the object described above according to the present invention, there is provided a method, which comprises the steps of inserting through the subclavian vein into the right atrium an inspection catheter provided with a pair of inspection electrodes at the leading end thereof and a slidably built-in guidewire, causing the inspection catheter to explore the endocardium of the atrium thereby to determine the optimum position for a pacemaker electrode, pushing the guidewire into the inspection catheter to form a loop at the optimum position thus determined within the atrium, piercing a double lumen needle through the chest wall in the direction of the loop of the guidewire, passing an induction steel wire through the double lumen needle, drawing the guidewire to contact the loop of the guidewire thereby to catch firm hold of the inserted end of the steel wire, withdrawing completely the inspection catheter together with the steel wire, releasing the inspection catheter from the steel wire and instead, tying a pervenous pacemaker electrode to the steel wire by the medium of a sutural thread, drawing the tail end of the steel wire remaining on the outer exposed side of the double lumen needle pierced through the chest wall to introduce the pacemaker electrode into the interior of the atrium until the pacemaker electrode is brought into contact with the endocardium of the right atrium and thereafter the sutural thread fixed to the pacemaker electrode is withdrawn all the way through the skin, removing the lumen needle from the chest wall and suturing the sutural thread on the subcutaneous tissue thereby to keep the pacemaker electrode attached tightly on the endocardium of the atrium.

Although the method of this invention necessitates advanced surgical technique on the part of the surgeon in the process in which the inspection catheter designed for detection of endocardial potential is introduced inside the right atrium and operated to explore the endocardium of the right atrium and determine the optimum position for the permanent pervenous electrodes, it enjoys an advantage that, once the optimum position is determined, the fixation of the pervenous electrodes can be accomplished with a comparatively simple technique, the step of again guiding the pervenous electrodes to the predetermined optimum position and fastening it to the optimum position, which has proved to be the most troublesome work in the conventional surgical technique is no longer required and the possibility of exposing the patient to surgical incursion is minimized.

The method of this invention can be practiced by using an inspection catheter which comprises a slender outer tube having a pair of inspection electrodes at the leading end thereof, guidewire slidably built in the outer tube and tied to the leading end of the tube and a double lumen needle which is adapted to introduce an induction steel wire doubly folded into the right atrium.

The other objects and characteristic features of the present invention will become apparent from a detailed description of the invention to be given hereinafter with reference to the accompanying drawing.

BRIEF EXPLANATION OF THE DRAWING

FIG. 1 is a partially cutaway overall view of one preferred embodiment of the inspection catheter for the detection of endocardial potential according to the present invention.

FIGS. 2 and 3 are sectioned views showing in detail the leading end of the catheter of FIG. 1 in the states assumed respectively after and before the guidewire forms a loop.

FIG. 4 is an enlarged sectioned view of the tail end of the catheter of FIG. 1.

FIGS. 5–12 are explanatory diagrams showing the steps which are involved in working the method of this invention for the fixation of the pervenous electrodes inside the right atrium in the order in which they are performed.

DETAILED DESCRIPTION OF THE INVENTION

Figure 5:
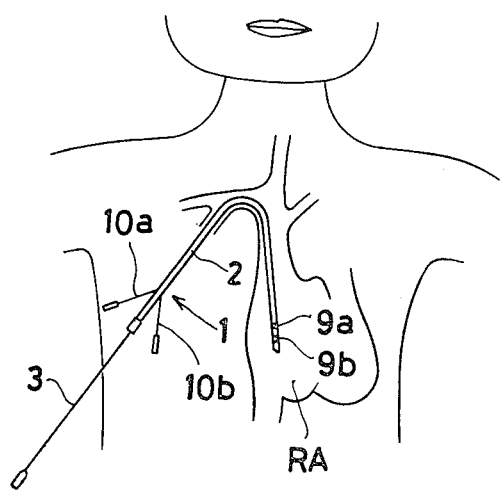

The method of the present invention for the fixation of the pervenous electrodes in the atrial pacing necessitates use of an inspection catheter designed for the detection of endocardial potential, a pair of pervenous electrodes designed for permanent fixation onto the endocardium of the right antrium, a double lumen needle adapted to pierce through the chest wall into the right atrium and an induction steel wire doubly folded.

First, the inspection catheter designed for the detection of endocardial potential will be described with reference to FIGS. 1 through 4.

This catheter 1 is used for the purpose of determining the optimum position for the fixation of the pervenous electrodes inside the right atrium by detecting the stimulating threshold through probing contact of the anterior and lateral walls of the right atrium and by measuring the endocardial potential. As illustrated, the inspection catheter comprises a long slender outer tube 2 and a flexible guidewire 3 slidably passing through the outer tube, with the leading end of the guidewire 3 tied to the leading end of the outer tube. When the rear portion 3' of the guidewire 3 which extends outwardly from the tail end of the outer tube is pushed into the outer tube in the same way as in a release cable for a camera, the leading portion of the guidewire 3 is pushed out of the leading end of the outer tube. In the guidewire, a fine steel wire 3b provides support from inside for a covering tube of a coiled wire 3a and helps the covering tube 3a slide smoothly inside the outer tube 2 at the time that the catheter is put to use. The fine steel wire 3b further serves the purpose of expanding the loop 4 which the guidewire 3 forms outside the leading end of the outer tube 2 when the rear portion of the guidewire is pushed into the outer tube.

A tough, very thin string 6 is passed through the opening of an obliquely cut end 5 of the outer tube 2 and a hole 5' perforated immediately behind the base of the cut end and the opposite ends of this thin string 6 are secured to the leading end of the covering tube 3a. The leading ends of the outer tube 2 and the guidewire 3 are united to each other in the manner just described. At the tail ends of the outer tube 2 and the guidewire 3, there may be provided squeezing pieces 7, 8 similar to those in a release cable for a camera to facilitate the operation of the inspection catheter. The squeezing pieces 7, 8 are desired to be made of a plastic material to preclude adhesion of blood.

When the rear portion 3' of the guidewire 3 which extends outwardly from the tail end of the outer tube 2 is pushed down toward the tail end of the outer tube, the leading end portion of the guidewire 3 is forced out in a manner folded backwardly from the leading end of the outer tube because the leading end of the guidewire 3 is secured by a string 6 to the base of the obliquely cut end 5 of the outer tube, causing the guidewire 3 to form a loop of a size corresponding to the extent of the push given to the rear portion 3' outside the leading end of the outer tube. When the rear portion 3' is pulled away from the rear end of the outer tube after the guidewire 3 has formed the loop, the exposed leading end portion of the guidewire retracts into the leading end portion of the outer tube and the loop 4 gradually diminishes and eventually disappears. The obliquely cut end 5 formed at the leading end of the outer tube 2 facilitates the formation of the loop of the guidewire mentioned above and the smooth retraction of the formed loop. The cut end is so formed as to allow easy insertion of the catheter through a hole incised in the vein via the cepharic vein into the right atrium. What is most important about the cut end of the outer tube is the fact that the leading end of the guidewire is tied to one lateral side of the leading end of the outer tube. When the guidewire 3 is composed of a covering tube 3a and a fine steel wire 3b passing through the covering tube and the leading end of the fine steel wire 3b is fastened to the covering tube 3a as in the case of the present preferred embodiment, the formation of the loop and the retraction of the formed loop can be facilitated by causing the leading end of the fine steel wire to be fixed onto the covering tube slightly back from the leading end of the covering tube so that the leading end portion of the guidewire is formed solely of covering tube and, therefore, is allowed to enjoy great freedom of flexing. The loop can always be formed in a fixed direction in relation to the outer tube owing to the obliquely cut end 5 and the string 6 by which the guidewire and the outer tube are connected at their leading ends with each other.

The inspection catheter is provided outside the leading end portion of the outer tube 2 with a pair of electrodes 9a, 9b. These electrodes 9a, 9b can be formed by having conductive pieces tightly wound on the outer surface of the outer tube 2, for example. In the present preferred embodiment, lead wires 10a, 10b connected respectively to the electrodes 9a, 9b extend backwardly in the wall of the outer tube 2 and drawn out of the tail end of the outer tube 2. To the rear ends of the lead wires 10a, 10b are optionally attached suitable connectors 11a, 11b for electrical connection to a measuring instrument. The aforementioned lead wires 10a, 10b are not necessarily required to be extended in the wall of the outer tube 2. They may be extended on the outer surface of the outer tube or they may be extended inside the hollow interior of the outer tube in such a way as not to interfere with the sliding of the guidewire. The portions of the lead wires 10a, 10b which are drawn out of the tail end of the outer tube 2 may be covered with an insulating coat and the portions where the lead wires depart from the tail end may be wrapped in an insulating tape 10 as occasion demands.

The fixation of the pacemaker electrodes to the endocardium of the right atrium of a given patient by means of the inspection catheter of this invention is carried out by the following procedure.

As described previously, a local incision is formed directly below the center of the patient's clavicle, and the catheter 1 is inserted through the subclavian vein into the right atrium RA until the aforementioned electrodes 9a, 9b provided at the leading end portion of the outer tube 2 comes into contact with the endocardium of the right atrium RA (FIG. 5). The rear ends of the lead wires 10a, 10b are connected to an external instrument for the measurement of endocardial potential of the right atrium. Further, the rear ends of the lead wires 10a, 10b are connected to an extracorporeal pacemaker so as to forward electric current to the right atrium and measure the electrical stimulating threshold of the right atrium. The measurement of the endocardial potential and the measurement of the electrical stimulating threshold are continued while the leading end portion of the catheter is moved about inside the right atrium and the electrodes 9a, 9b are consequently brought into contact with various regions of the endocardium of the right atrium. In this manner, the optimum position for the fixation of the pacemaker electrodes is determined.

Figure 6:
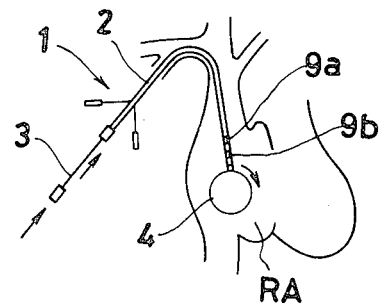

After the optimum position has been determined, the movement of the catheter is discontinued and the leading end portion thereof is kept at the optimum position. Then, the rear portion of the guidewire 3 is pushed down into the outer tube 2 so that the leading end portion of the guidewire forms a loop 4 of a desired size at the leading end of the outer tube inside the right atrium as described previously (FIG. 6). Subsequently, a skin incision of approximately 2 cm is formed at the righthand extremity of the sternum in the fourth intercostal space. Through this skin incision, a double lumen needle 12 is pierced in the direction of the leading end portion of the outer tube inside the right atrium under fluoroscopic observation and the center of the loop 4 is positioned at the leading end of the needle by slightly pulling out the outer tube.

Figure 7:
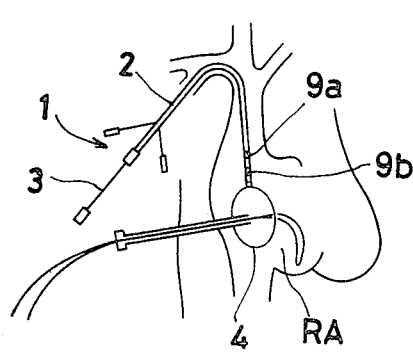
Figure 8:
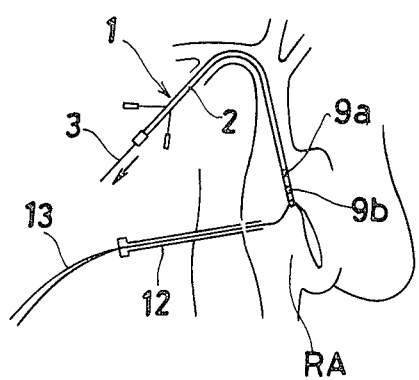

Thereafter, a doubly folded induction steel wire 13 used for the fixation of the pacemaker electrodes is inserted, with the folded end first, into the double lumen needle 12 until the folded end of the induction steel wire 13 passes the vicinity of the center of the loop 4 inside the right atrium (FIG. 7). After that, the guidewire 3 is pulled backwardly relative to the outer tube 2 so as to contract the loop 4. Eventually, the guidewire 3 is retracted via the leading end of the outer tube with the result that the induction steel wire 13 is caught fast between the leading ends of the guidewire 3 and the outer tube 2 (FIG. 8). Then, the catheter is completely extracted from the subclavian vein (FIG. 9), so that the firmly gripped end of the induction steel wire 13 is drawn out of the body. At this point, the catheter is released from the induction steel wire 13. Now, the leading end of an endocardial lead 14' which has a pair of pacemaker pervenous electrodes 14 disposed in an exposed state on the outer surface of the leading end thereof is connected with a sutural thread to the induction steel wire 13 (FIG. 10), and rear end portion of the induction steel wire 13 protruding from the exposed end of the double lumen needle 12 is pulled away from the needle 12 so as to draw the endocardial lead 14' into the interior of the right atrium (FIG. 11). As the result of the pull of the induction steel wire 13, the induction steel wire is first drawn out of the double lumen needle 12 and a part of the thread 15 is drawn out of the needle 12 subsequently. Shortly thereafter, the pull of the thread 15 through the double lumen needle 12 comes to a halt when the leading end of the endocardial lead 14' connected to the sutural thread collides into the leading end of the double lumen needle 12 which passes into the cavity of the right atrium. At this point, the double lumen needle 12 is drawn out of the patient's body. Then the thread 15 is sutured on the subcutaneous tissue at the righthand extremity of the sternum in the fourth intercostal space. A pacemaker 16 connected to the end of the endocardial lead 14' is implanted in the chest wall (FIG. 12).

Since the inspection catheter 1 forms the loop at a predetermined optimum position and the double lumen needle 12 is pierced in the direction of the center of the loop, the pervenous electrodes 14 disposed at the leading end of the endocardial lead 14' which has been drawn by the induction steel wire 13 and the sutural thread 15 and brought into collision with the leading end of the double lumen needle will consequently come into contact with the endocardium of the right atrium at or near the optimum position determined in advance by the inspection catheter.

According to the present invention, therefore, the pacemaker pervenous electrodes can be fixed at the optimum position determined in advance on the endocardium of the right atrium by having the electrodes 9a, 9b disposed as close to the leading end of the outer tube 2 as permissible. Since the determination of the optimum position for the fixation of the pervenous electrode and the fixation of the pervenous electrode at that predetermined optimum position are realized by having the inspection catheter inserted just once into the right atrium, the time and labor required for the attachment of the pacemaker can be notably saved by the method of the present invention.

In the preferred embodiment described above, one pair of electrodes 9a, 9b are used and the measurement of endocardial potential and that of stimulating threshold are effected by suitably switching the connection of the lead wires 10a, 10b. Instead, there may be incorporated two pairs of electrodes, one of the two pairs used for the measurement of endocardial potential and the other pair for the measurement of stimulating threshold.

Although the present invention has been described with reference to one illustrated preferred embodiment, it is not limited to this preferred embodiment but may be practiced in various modifications without departing from the spirit of this invention.

What is claimed is:

1. A method for the fixation of pacemaker electrodes of an atrial pacemaker in the right atrium of a given patient, which method comprises the steps of:

inserting through the subclavian vein into the right atrium an inspection catheter composed of a slender outer tube having at least a pair of electrodes at the leading end thereof and a flexible guidewire slidably built in the outer tube and having the leading end connected to the leading end of the outer tube;

operating the inserted catheter to explore the endocardium of the right atrium, thereby to determine the optimum position for the fixation of the pacemaker electrodes by measuring the endocardial potential through probing contact by said electrodes of the endocardium of the right atrium;

causing the guidewire, subsequently to the determination of the optimum position, to be pushed into the outer tube to form a loop of a desired size at the leading end of the outer tube inside the right atrium under the state of keeping the leading end portion of the guidewire at the optimum position;

piercing a double lumen needle through the chest wall in the direction of the leading end portion of the outer tube under fluoroscopic observation;

inserting an induction wire serving to guide the pacemaker electrodes into the atrium through the double lumen needle into the interior of the right atrium;

pulling backwardly the guidewire relative to the outer tube to contract the loop for thereby causing the induction wire to be caught fast by the leading end of the inspection catheter;

extracting the inspection catheter from the right atrium and the subclavian vein along with the part of the induction wire caught by the leading end of the inspection catheter;

releasing the inspection catheter from the induction wire;

connecting the induction wire with a sutural thread disposed at the pacemaker electrodes;

causing the rear end of the induction wire protruding from the exposed end of the double lumen needle to be drawn out of the double lumen needle so as to draw the pacemaker electrodes into the interior of the right atrium;

removing the double lumen needle from the chest wall; and suturing the sutural thread on the subcutaneous tissue, thereby to fix the pacemaker electrodes in the right atrium.

2. An inspection catheter for the fixation of pacemaker electrodes in the right atrium of a given patient, which comprises:

a long slender outer tube having a leading end, a tail end and at least one pair of electrodes disposed in an exposed state on the outer surface of the leading end of the outer tube, and lead wires having leading ends and tail ends, said lead wires connected at their leading ends respectively to the electrodes and extended toward the tail end of the outer tube; and a flexible guidewire having a length greater than that of the outer tube, and having a leading end fixedly connected to the leading end of the outer tube and slidably disposed in the outer tube so that the guidewire is pushed out of the leading end of the outer tube by pushing down into the outer tube a rear portion of the guidewire protruding from the tail end of the outer tube, the leading end remaining fixed to the tube thereby to form a loop for catching hold of an induction wire serving to guide pacemaker electrodes into the right atrium.

3. The inspection catheter according to claim 2, wherein the lead wires connected to the electrodes extend backwardly in the wall of the outer tube and further external terminals are provided at the tail ends of the lead wires.

* * * * *